United States Patent
Graf et al.

(10) Patent No.: US 7,751,896 B2
(45) Date of Patent: Jul. 6, 2010

(54) ACTIVE RETINA IMPLANT WITH A MULTIPLICITY OF PIXEL ELEMENTS

(75) Inventors: Heinz-Gerhard Graf, Magstadt (DE); Alexander Dollberg, Dortmund (DE); Bernd Hoefflinger, Sindelfingen (DE); Wilfried Nisch, Tuebingen (DE); Hugo Haemmerle, Tuebingen (DE); Alfred Stett, Reutlingen (DE); Martin Stelzle, Reutlingen (DE); Eberhart Zrenner, Tuebingen (DE)

(73) Assignee: Retina Implant AG, Reutlingen (DE)

( * ) Notice: Subject to any disclaimer, the term of this patent is extended or adjusted under 35 U.S.C. 154(b) by 672 days.

(21) Appl. No.: 11/305,920

(22) Filed: Dec. 19, 2005

(65) Prior Publication Data
US 2006/0184245 A1    Aug. 17, 2006

Related U.S. Application Data

(63) Continuation of application No. PCT/EP2004/005975, filed on Jun. 3, 2004.

(30) Foreign Application Priority Data
Jun. 23, 2003  (DE) ................... 103 29 615

(51) Int. Cl.
*A61F 2/14*    (2006.01)
(52) U.S. Cl. .......................... 607/54; 623/6.63
(58) Field of Classification Search ............ 607/53, 607/54; 623/6.63
See application file for complete search history.

(56) References Cited

U.S. PATENT DOCUMENTS

| 5,024,223 A | 6/1991 | Chow |
| 5,608,204 A | 3/1997 | Hofflinger et al. |

(Continued)

FOREIGN PATENT DOCUMENTS

DE    42 09 536    9/1993

(Continued)

OTHER PUBLICATIONS

International Search Report for PCT/EP2004/005975, mailed on Oct. 27, 2004, 3 pages.

(Continued)

*Primary Examiner*—Carl H Layno
*Assistant Examiner*—Paula J Stice
(74) *Attorney, Agent, or Firm*—Morrison & Foerster LLP

(57) ABSTRACT

An active retina implant has a multiplicity of pixel elements that convert incident light into electric stimulation signals for cells of the retina with which stimulation electrodes are to make contact. Each pixel element is provided with at least one image cell that converts incident light into electric signals, there being provided at least one amplifier whose input is connected to the image cell and whose output is connected to at least one stimulation electrode to which it supplies a stimulation signal. Also provided is an energy supply which provides externally coupled external energy as supply voltage for the image cells and the amplifiers. The image cell has a logarithmic characteristic according to which incident light of specific intensity is converted into electric signals of specific amplitude. The stimulation signal is supplied in the form of analog voltage pulses of specific pulse length and pulse spacings, the pulse amplitude being a function of the intensity of the incident light.

22 Claims, 6 Drawing Sheets

U.S. PATENT DOCUMENTS

| | | | |
|---|---|---|---|
| 5,895,415 A | 4/1999 | Chow et al. | |
| 6,298,270 B1 | 10/2001 | Nisch et al. | |
| 6,393,327 B1 * | 5/2002 | Scribner | 607/54 |
| 6,458,157 B1 * | 10/2002 | Suaning | 623/6.63 |
| 6,804,560 B2 | 11/2002 | Nisch et al. | |
| 2002/0091421 A1 * | 7/2002 | Greenberg et al. | 607/54 |
| 2002/0177895 A1 * | 11/2002 | Nisch et al. | 623/5.11 |
| 2006/0069416 A1 * | 3/2006 | Nisch et al. | 607/54 |

FOREIGN PATENT DOCUMENTS

| | | |
|---|---|---|
| DE | 429536 | 9/1993 |
| DE | 197 05 988 | 4/1998 |
| DE | 199 21 399 | 11/2000 |
| EP | 0 460 320 | 12/1991 |
| EP | 1 239 666 | 9/2002 |

OTHER PUBLICATIONS

Stelzle et al., Biomedical Microdevices (2001) 3:133-142.
English translation of the International Preliminary Report on Patentability for PCT/EP2004/005975, 5 pages.

* cited by examiner

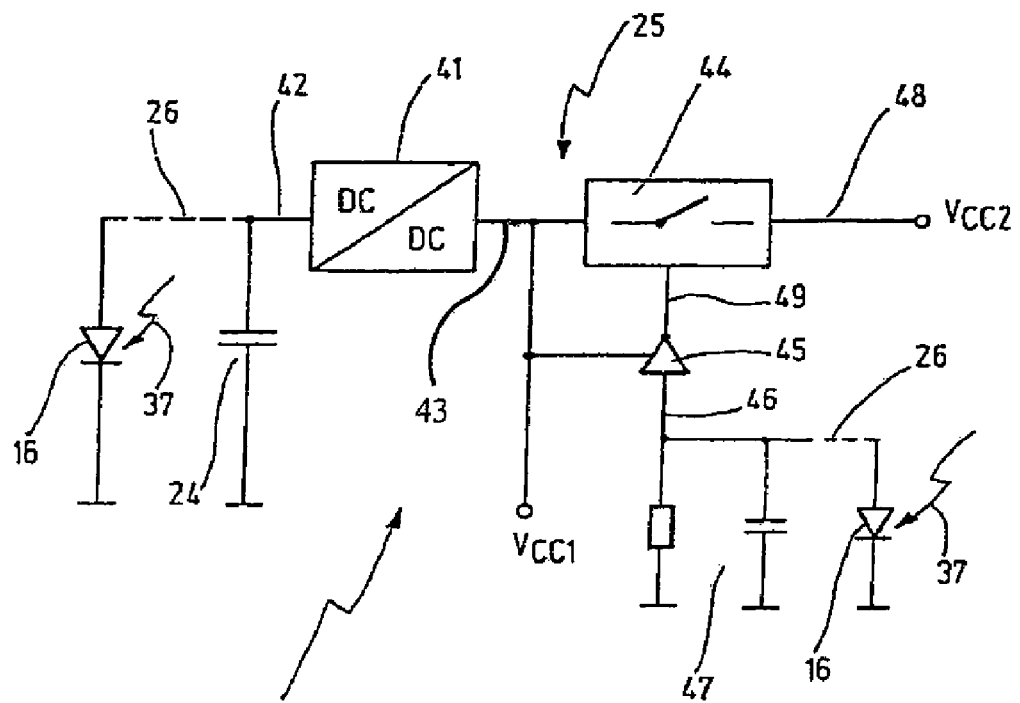
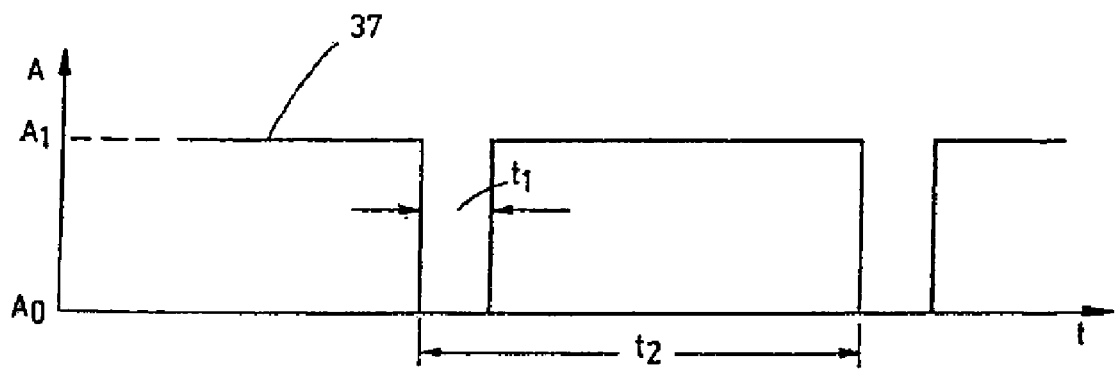
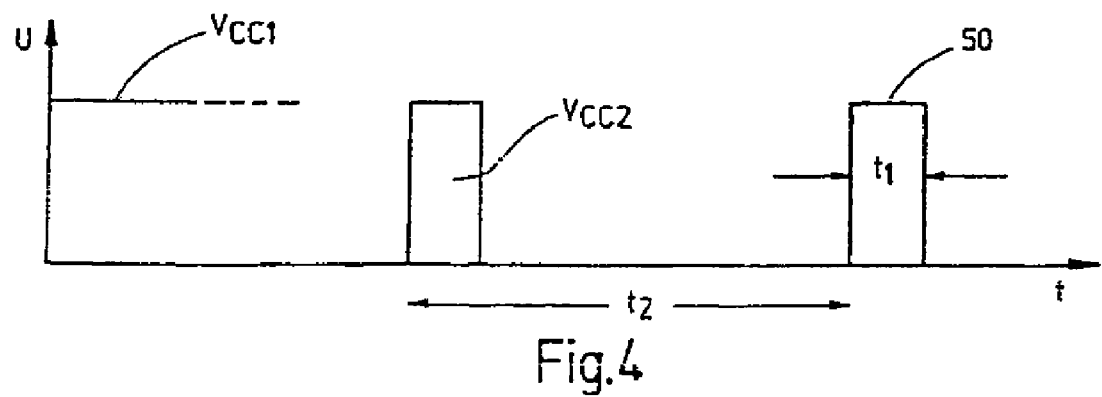

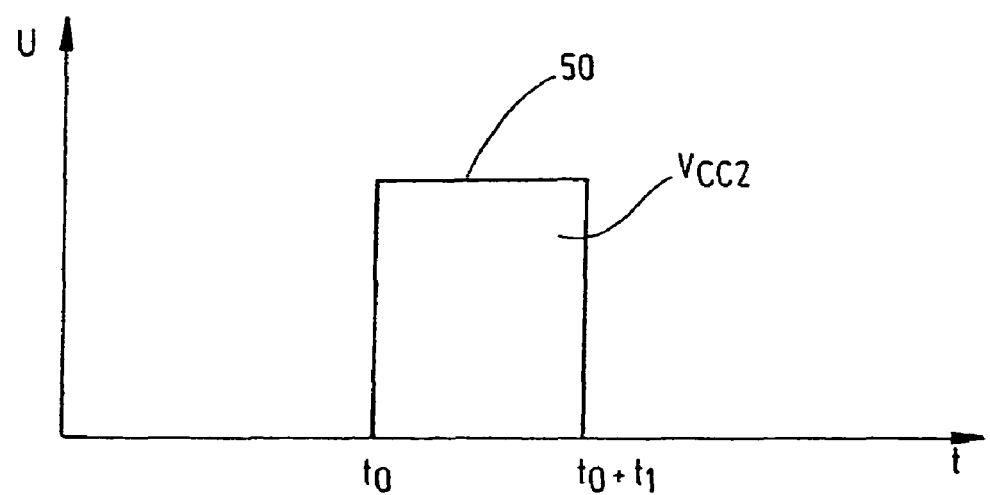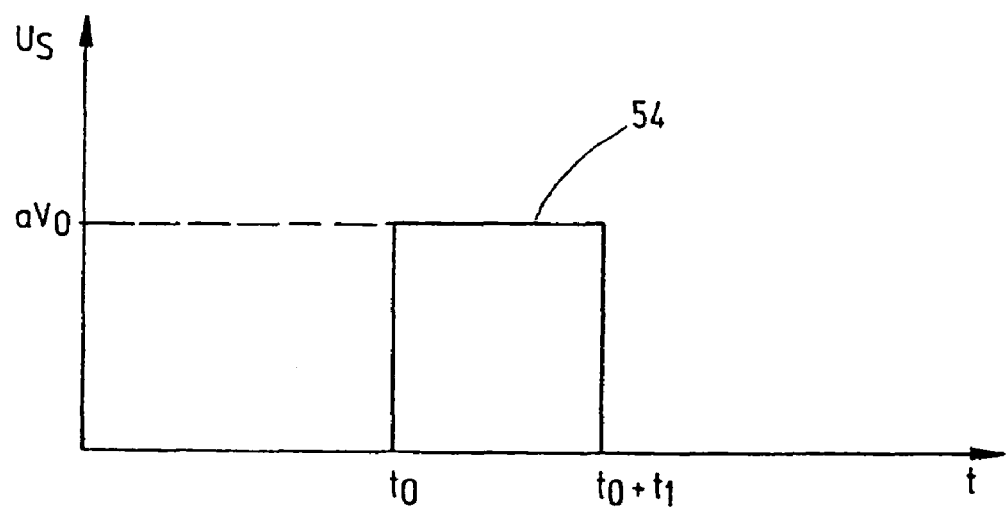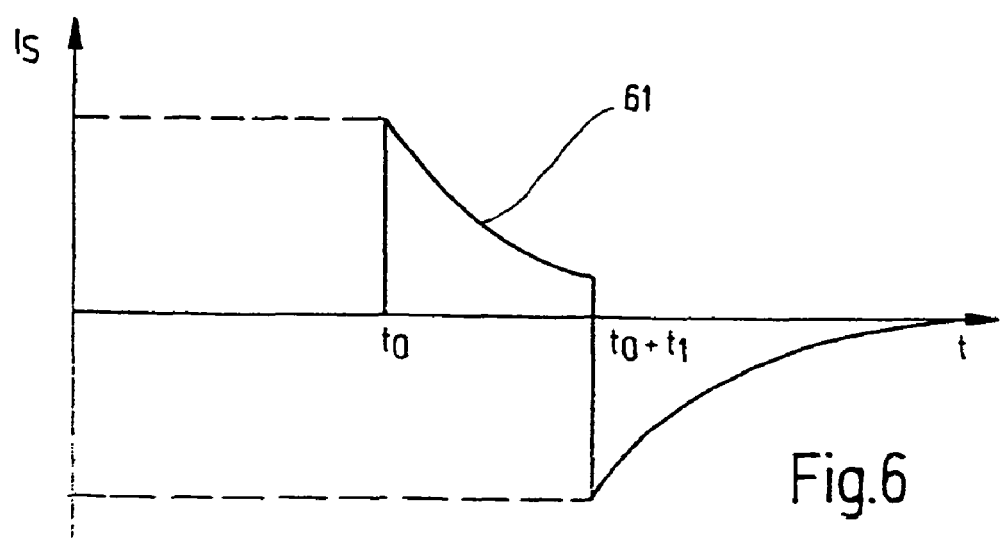
Fig.6

15 US 7,751,896 B2

ACTIVE RETINA IMPLANT WITH A MULTIPLICITY OF PIXEL ELEMENTS

RELATED APPLICATION

This is a continuation application of International Patent Application PCT/EP2004/005975, filed Jun. 3, 2004, designating the United States and published in German as WO 2005/000395 A1, which claims priority of German application No. 103 29 615.8, filed Jun. 23, 2003, both of which are incorporated herein by this reference.

BACKGROUND OF THE INVENTION

1. Field of the Invention

The present invention relates to an active retina implant with a multiplicity of pixel elements that convert incident light into electric stimulation signals for cells of the retina to be contacted with stimulation electrodes, each pixel element having at least one image cell that converts incident light into electric signals, and having at least one amplifier whose input is connected to the image cell and whose output is connected to at least one stimulation electrode to which it supplies a stimulation signal, and with an energy supply which provides externally coupled external energy as supply voltage for the image cells and the amplifiers.

2. Related Prior Art

Such a retina implant is disclosed, for example, in DE 197 05 988 A1.

The known retina implant serves the purpose of counteracting a loss of visual faculty based on retina degenerations. The basic idea here is to implant in the region of a patient's degenerated retina a microelectronic stimulation chip that is intended to replace the function of, for example, degenerated photoreceptors. The stimulation chip has a multiplicity of pixel elements that generate electric pulses in the region of the retina as a function of the incident visible light, and in so doing stimulate cells in the retina.

The retina implant can be mounted on the retina as an epiretinal implant, or else it can be inserted in or under the retina as a so-called subretinal implant.

A subretinal implant is disclosed, for example, in EP 0 460 320 A2. With this implant, the impinging ambient light is said to be sufficient for producing the required stimuli for the cells in the retina. Reference is made to this document for the precise placing of a subretinal retina implant.

In DE 197 05 988 A1 mentioned at the outset, a subretinal implant is described that is provided with a photovoltaic layer that is active for nonvisible electromagnetic radiation, the stimulation signals being switched locally by utilizing the voltage generated by the photovoltaic layer. The known implant is based on the idea of using electromagnetic radiation from the nonvisible spectral region, specifically infrared radiation, to provide an external energy for the stimulation chip. The photovoltaic layer acts in this case like a type of amplifier for the signals generated by the incident visible light. As a consequence of this, stimulation signals of adequate intensity can be generated even given weak light conditions in the visible spectral region.

However, the problem arises with the known retina implant of transforming the incident visible light into corresponding electric stimulation signals over a large intensity range that comprises a number of powers of ten in natural light conditions.

Against this background, DE 199 21 399 A1 describes a retina implant having at least one pixel element that acts as reference element, the amplifier forming the difference between the output signals of the reference element and the image cell that detects the local brightness. The aim in this way is to adapt the stimulation signal thus generated to the ambient brightness.

The article by Stelzle et al.: "Electrical Properties of Micro-Photodiode Arrays for Use as Artificial Retina Implant", Biomedical Micro Devices 3:2, 133-142, 2001 is concerned with the problems of transmitting stimulation signals via the stimulation electrodes to cells of the retina with which contact is to be made. The authors report that the coupling between the stimulation electrode and the tissue is of a capacitive nature such that only transient signals can be used for the stimulation. This capacitive coupling is based on the fact that as a consequence of electrode polarization a capacitance (Helmholtz double layer) is formed in the eye at the interface between electrode and electrolyte. The authors show that for a passive implant, that is to say an implant such as is described in the EP 0 460 320 A2 mentioned at the outset, pulsing of the visible useful light leads to a limit cycle in which a balanced charge transport into the capacitance and out of the latter again results. In order to solve the problems associated with the passive implant, the authors propose to use light pulses with a specific pulse rate. Furthermore, it is said to be desirable to use an external energy supply in order to generate the stimulation current. They also recommend the use of an active current sink in order to reduce the mean electrode polarization. However, they mention that it is very possible that a complete discharge of the electrode capacitance cannot be achieved because of the pulsed excitation.

SUMMARY OF THE INVENTION

In view of the above, it is an object of the present invention to improve the active retina implant mentioned at the outset with the aid of simple circuitry means in such a way as to achieve an effective transformation of the incident light into the stimulation signals so that the cells in the retina can be effectively stimulated even given differing ambient lighting.

In the case of the retina implant mentioned at the outset, this object and other objects are achieved according to the invention on the one hand in that the image cell has a logarithmic characteristic according to which incident light of specific intensity is converted into electric signals of specific amplitude.

The object underlying the invention is achieved completely in this way.

The logarithmic image cell, which has been known as such for many years from DE 42 09 536 A1, for example, has a logarithmic amplifier response that has been found by the inventors to resemble the photosensitivity of the eye, and can therefore be used particularly efficiently as an image cell. It is possible in this way to convert a large brightness range into stimulation signals even without a reference element and reference amplifier, thus enabling vision with adequate contrast both with low and with high ambient lighting.

On the other hand, the object is achieved in the case of a retina implant mentioned at the outset in that the stimulation signal is supplied in the form of analog voltage pulses of specific pulse length and pulse spacings whose amplitude is a function of the intensity of the incident light.

The object underlying the invention is completely achieved in this way, as well.

The inventors of the present application have found, specifically, that it is also possible to output analog voltage pulses to the cells in the retina via the stimulation electrodes when the aim is to achieve an adequate stimulation of the cells. The inventors are therefore not traveling directly on the usual road of using current pulses with charge compensation, but are making use of a voltage control, although this ought to pose problems on the basis of a prejudice in the prior art because of the electrode polarization.

However, the inventors have found that the voltage control can be implemented very simply in terms of circuitry and that the problems with the electrode polarization can be avoided nevertheless given correct design.

It is a further object to use the two measures, that is to say the image cell with the logarithmic characteristic, and the voltage control jointly. Specifically, because of the low outlay on circuitry it is possible to increase the density of the pixel elements and thus of the stimulation electrodes considerably such that a better spatial resolution is achieved here overall than is possible with the complicated circuits from the prior art. This higher density leads to a more effective stimulation of the cells in the retina, since the local ratio between the number of stimulation electrodes and the number of cells to be excited becomes larger.

It is particularly preferred in this case when the output of the amplifier is connected to a controllable discharge circuit.

An increasing electrode polarization can be decreased again in a targeted fashion via this discharge circuit, thus preventing the charge, and thus the voltage in the interface capacitance, from increasing more and more, something which would lead contrariwise to the fact that the stimulation signal could be transmitted in an ever worsening fashion to the cells in the retina.

It is another objective that pulse length and pulse spacing are determined via the externally coupled external energy.

It is advantageous in the case of this measure that pulse length and pulse spacing, that is to say pulse rate, need not be generated via a mechanical chopping of the visible useful light, as in the prior art, or via frequency generators to be provided on the retina implant. The outlay on circuitry of the retina implant is also kept considerably low in this way.

A further advantage consists in that, after the insertion of the retina implant, pulse length and pulse spacing can be adapted individually to the physiological conditions for the respective patient. It is also possible to change pulse length and pulse spacing as a function of the respective lighting conditions. In other words, owing to this measure the external energy supply simultaneously also effects a control of the mode of operation of the implant.

Here, the external energy supply can be, for example, coupled IR light, or else inductively coupled energy, for example in the RF region.

It is preferable, furthermore, when the discharge circuit is controlled at the end of a voltage pulse in such a way that the output of the amplifier is connected to a discharging potential.

It is advantageous here that the electrode polarization is restored automatically at the end of each stimulating voltage pulse, since the capacitance between the stimulation electrode and surrounding tissue is discharged. Each new voltage pulse therefore encounters a completely discharged capacitor such that at the start of the voltage pulse a high stimulation current can pass through the capacitor into the tissue and to the cells of the retina. This current decreases over time because of the increasing voltage in the interface capacitor. After the voltage pulse has been switched off, the output of the amplifier is then connected to the discharging potential that as a rule is the electric mass of the retina implant. This results in a large discharging current that again completely discharges the interface capacitance.

It has proved that a pulse length of approximately 500 µs suffices in order to stimulate the cells in the retina adequately.

The initial strength of the current at making is determined in this case via the amplitude of the voltage pulse.

The pulse spacing is preferably 50 ms here, because a repetition frequency of 20 Hz has proved to be sufficient for nonflicking vision. This pulse spacing is also sufficient for completely restoring the electrode polarization.

It is still another object that the image cells are supplied with a first voltage that differs from a second voltage with which the amplifiers are supplied, the second voltage preferably being switched on with the pulse length and the pulse spacing.

It is advantageous here that the image cells are, for example, continuously supplied with the first voltage such that the electric signals of the image cells are continuously available and there is no need to wait for any settling processes. On the other hand, the amplifiers are supplied with the second voltage, which is switched on with the pulse length and the pulse spacing. The electric signals of the image cells are converted in this way into the voltage pulses via the clocked amplifier. This is particularly simple in terms of circuitry, because there is no need to switch an additional clock stage to the output of the amplifier—rather, the amplifier is switched on and then off again in step with the voltage pulses. Since the timed switching on and off of the second voltage is derived from the externally coupled external energy, the advantage already mentioned above results that, specifically, the retina implant can be controlled via the external energy.

It is also preferred when the discharge circuit is connected to a third voltage that is derived from the second voltage.

It is advantageous here that the third voltage, which activates the discharge circuit, is generated as the second voltage is switched off.

Thus, the respective amplifier is switched on and the positive edge of the voltage pulse is generated in this way as the second voltage is switched on. The discharge circuit is activated as a second voltage is switched off, and this supplies the negative edge of the voltage pulse.

Overall, this type of control of the retina implant offers the advantage that all the switching operations in the implant are controlled via an appropriate modulation of the externally coupled external energy, there being no need even for these purposes of timers or frequency generators in the implant.

The implant described so far is therefore of very simple design in terms of circuitry, and so it is possible to achieve a high density of the individual elements and thus also of the stimulation electrodes. This high density enables a good, locally triggered stimulation of cells in the retina, an effective stimulation of the cells being possible because of the pulsed excitation and of the respectively complete restoration of the electrode polarization. Because of the logarithmic characteristic, the novel retina implant can also cover many powers of ten of image brightness.

It is, however, preferred when each pixel element has a logarithmic image cell for local image brightness, and each pixel element is assigned at least one logarithmic image cell for global brightness, the amplifier preferably being designed as a difference amplifier of which one input is connected to the image cell for local image brightness, and of which the other input is connected to the image cell for global brightness.

This measure is known per se from the DE 199 21 399 A1 mentioned at the beginning, albeit for image cells with a linear characteristic.

When this "differential amplifier principle", in the case of which the difference between the local image brightness and the global brightness, taken over one or more reference elements, is amplified and passed on as stimulation signal, is used with logarithmic image cells, the particular advantage results that a pure contrast amplification is present here and the mean brightness is eliminated by forming the difference, because it is only an additive variable in the logarithm of the image brightness.

In view of the above, the present invention likewise relates to the use of an image cell with a logarithmic characteristic for a pixel element of an active retina implant that has a multiplicity of pixel elements that convert incident light into electric stimulation signals for cells of the retina with which stimulation electrodes are to make contact.

Further advantages follow from the description and the attached drawing.

It goes without saying that the features named above and those still to be explained below can be used not only in the respectively specified combination, but also in other combinations or on their own without departing from the scope of the present invention.

BRIEF DESCRIPTION OF THE DRAWINGS

An embodiment of the invention is illustrated in the drawing and explained in more detail in the following description. In the drawing:

FIG. 3 shows the block diagram of the power supply unit for the retina implant from FIG. 1;

FIG. 4 shows the derivation of the second voltage from the externally coupled IR light;

FIG. 6 shows the voltage and current characteristics for the pixel element from FIG. 5;

DESCRIPTION OF A PREFERRED EMBODIMENT

Figure 1:
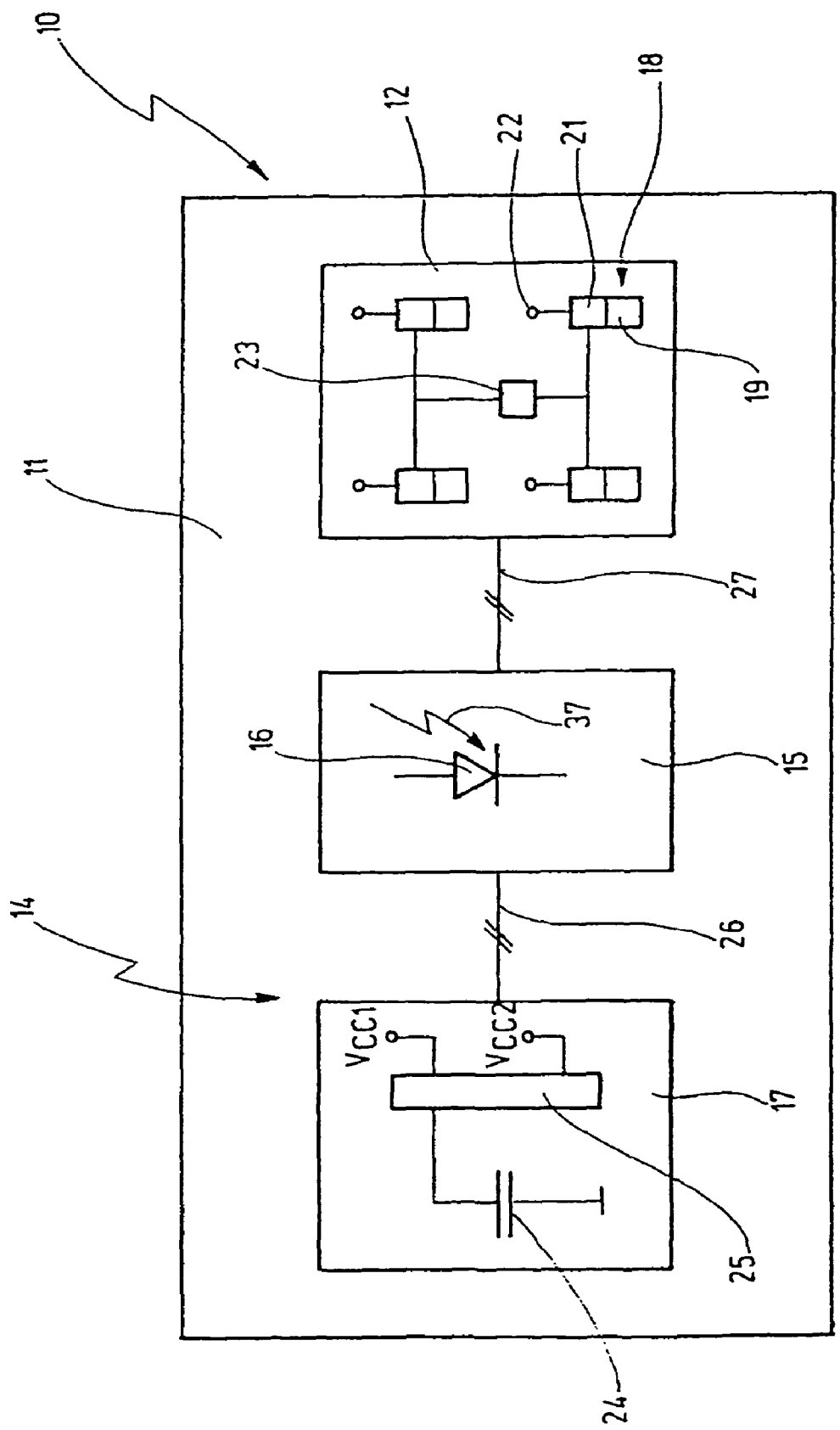
FIG. 1 shows a schematic of the novel retina implant in illustration not true to scale.

FIG. 1 is a schematic of an active retina implant 10, the dimensions not being reproduced true to scale.

The retina implant 10 is constructed on a flexible film 11 on which a stimulation chip 12 and an energy supply 14 are arranged. The energy supply 14 comprises an IR receiver 15 that includes one or more photovoltaic elements 16 that convert impinging IR light into electric voltage. The external energy thus injected is transferred to a power supply unit 17.

The stimulation chip 12 comprises, for example, pixel elements 18 that are arranged in rows and columns and of which only four are illustrated in FIG. 1, for the sake of clarity. Each pixel element 18 comprises a logarithmic image cell 19 for local image brightness, and an amplifier 21 that is connected at its output to a stimulation electrode 22. Furthermore, there is provided on the stimulation chip 12 an image cell 23 for global brightness that is connected to the amplifiers 21 of all the pixel elements 18 on the stimulation chip 12. It goes without saying that the stimulation chip 12 can comprise a number of global image cells 23, or else also only a single one thereof.

The power supply unit 17 has a storage element 24 in which the external energy picked up by the IR receiver 15 is stored.

The storage element 24 is connected to a circuit part 25 that generates two different voltage supplies $V_{cc1}$ and $V_{cc2}$ in a way yet to be described in more detail. The power supply unit 17, the IR receiver 15 and the stimulation chip 12 are connected to one another via lines 26 and 27.

Figure 2:
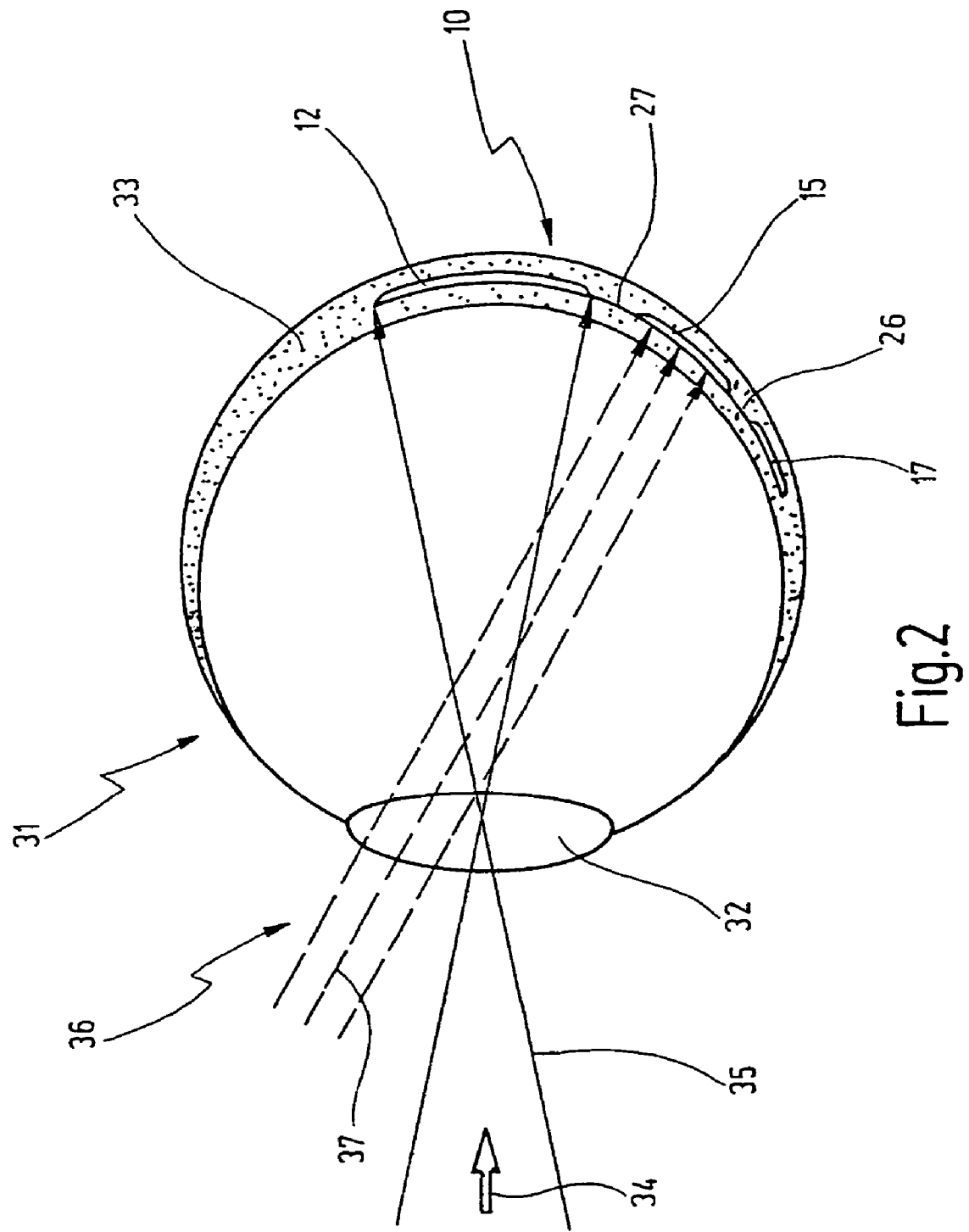
FIG. 2 shows a schematic of a human eye with inserted retina implant, likewise not true to scale.

The retina implant 10 from FIG. 1 is intended to be implanted into a human eye 31 that is illustrated in FIG. 2 in a highly schematic fashion. For the sake of simplicity, only the lens 32 is shown, together with the retina 33 into which the implant 10 has been implanted. The implant 10 is preferably inserted in, this case in the so-called subretinal space that is formed between the pigment epithelia and the photoreceptor layer. If the photoreceptor layer degenerates or is lost, the subretinal space is formed between the pigment epithelia and the layer of the bipolar cells and horizontal cells. In this case, the retina implant 10 is placed such that stimulation signals can be exerted on cells in the retina 33 via the stimulation electrodes 22 shown in FIG. 1.

Visible light that is indicated by an arrow 34 and whose beam path is to be seen at 35 is guided via the lens 32 onto the stimulation chip 12, where the visible light 34 is converted into electric signals that are transformed into stimulation signals via the amplifiers 21 from FIG. 1.

It is to be seen in FIG. 2 that the IR receiver 15 is situated outside the area of incidence of the visible light 34. External energy 36 in the form of beams of IR light 37 is directed onto the IR receiver 15, said IR light being converted in the IR receiver into an electric voltage that firstly passes via the lines 26 to the power supply unit 17 where it is used to generate appropriate supply voltages. These supply voltages then pass via the lines 26 and 27 to the stimulation chip 12 where they are used to convert the incident, visible light 34 into stimulation signals in a way still to be described in more detail.

The spatial separation of stimulation chip 12 and IR receiver 15 results in a spatial decoupling such that the undesired impairment of the image cells in the stimulation chip 12 by the IR light 37 is kept slight.

How the required supply voltages are generated from the IR light 37 will now be described with the aid of FIG. 3, where the power supply unit 17 from FIG. 1 is illustrated in more detail, but yet schematically.

The power supply unit 17 comprises a DC-DC converter that is connected at its input 42 to the storage element 24. This storage element 24 is connected via the lines 26, illustrated by dashes, to the photovoltaic element 16 that generates from the IR light 37 an electric voltage that is stored as charge in the storage element 24. From this charge, which represents a DC voltage, the DC-DC converter 41 generates at its output 43 a further DC voltage $V_{cc1}$, as is known per se for DC-DC converters.

The output 43 of the DC-DC converter 41 is, furthermore, connected to an electronic switch 44 that is closed and opened via an inverter 45. The inverter 45 is connected at its input to an RC element 47 and also to the photovoltaic element 16 via the lines 26 illustrated by dashes. At its output 48, the electronic switch 44 outputs a voltage $V_{cc2}$ that is pulsed, as will now be explained with the aid of FIG. 4.

Shown at the top in FIG. 4 is the time profile of the IR light 37 that is switched periodically for the period $t_1$ from the amplitude A1 to the amplitude A0. These "negative light pulses" of period $t_1$ are repeated at time intervals $t_2$. It goes without saying that the IR light 37 modulated in such a way during the period $t_1$ can either be switched off entirely, or else merely be lowered to a lesser intensity value.

This modulation of the IR light 37 is smoothed by the storage element 24 such that the supply voltage $V_{cc1}$ constantly takes a specific value as is shown at the bottom in FIG. 4.

Via the RC element 47, the modulated IR light 37 passes to the inverter 45 whose output 49 is an L signal as long as the IR light 37 is at intensity $A_1$. During this time, the electronic switch 44 is opened such that the supply voltage $V_{cc2}$ is at 0 V.

During the time interval $t_1$, the input 46 of the inverter 45 goes to L signal, which means that its output 49 goes to H signal and the electronic switch 44 closes. During the time interval $t_1$, the supply voltage $V_{cc2}$, for example, therefore goes to the same value as the supply voltage $V_{cc1}$. The output 48 of the electronic switch 44 therefore supplies voltage pulses 50 with a pulse length $t_1$ and a pulse spacing $t_2$.

It will now be explained with the aid of FIG. 5 how these voltage pulses 50 that are derived from the modulation of the IR light 37 are used in order to control the stimulation chip 12.

Figure 5:
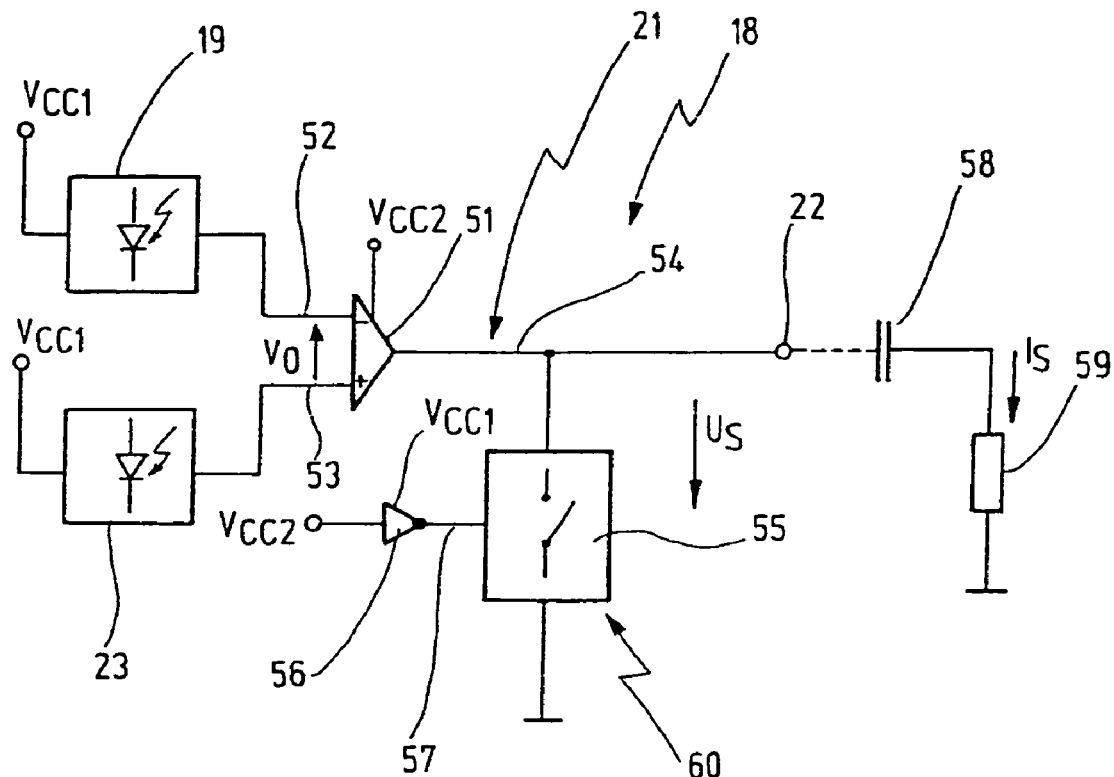
FIG. 5 shows the block diagram of an image cell for the stimulation chip of the retina implant from FIG. 1.

A pixel element 18 is illustrated in FIG. 5 in more detailed and yet schematic fashion.

The pixel element 18 comprises a differential amplifier 51 that is connected at its inverting input 52 to the image cell 19 for local image brightness. The differential amplifier 51 is connected at its non-inverting input 53 to the image cell 23 for global brightness.

The differential amplifier 51 is connected at its output 54 to the stimulation electrode 22. Furthermore, the output 54 is connected to an electronic switch 55 that is driven via an inverter 56 that supplies the inverted signal of the supply voltage $V_{cc2}$ at its output as third voltage 57. The image cells 19 and 23, and the inverter 56 are supplied with energy via the supply voltage $V_{cc1}$. By contrast, the amplifier 51 is supplied with energy via the supply voltage $V_{cc2}$.

Thus, a differential voltage $V_D$ that represents the difference between the output signals of the image cells 19 and 23 is present at the inputs 52, 53 of the differential amplifier 51.

During the period $t_2$, the differential amplifier 51 itself is respectively supplied with energy only for the period $t_1$ such that it outputs a stimulation signal $U_s$ at its output 54 only during the on time of the voltage pulses 50 from FIG. 4. This relationship is shown in FIG. 6.

Thus, during the interval from $t=t_0$ to $t=t_0+t_1$ there is present at the output 54 of the amplifier 51 a voltage pulse whose amplitude $aV_D$ corresponds to the intensity of the visible light falling onto the image cells 19, 23.

At the end of the voltage pulse 50, the inverter 56 goes to H signal at its output and closes the electronic switch 55, which in this way connects the output 54 to electrical ground.

As already mentioned at the outset, there is formed at the stimulation electrode 22 a Helmholtz double layer that ensures a capacitive coupling of the stimulation electrode 22 to the surrounding tissue in the retina. This capacitive coupling is indicated in FIG. 5 by a coupling capacitor 58 that is likewise connected to electrical ground via a resistor 59 that represents the stimulated tissue/the stimulated cells.

At the start of the voltage pulse 50, the amplifier 51 switches at its output 54 to the voltage $U_s=aV_D$, the result being that a stimulation current $I_S$ flows via the coupling capacitor 58 into the resistor 59, as is illustrated at the bottom in FIG. 6. The strength of the stimulation current $I_S$ now decreases exponentially, since the coupling capacitor 58 is recharged, something which is also denoted as electrode polarization. At the instant $t=t_0+t_1$, the voltage pulse 50 switches off again, which means that the supply voltage $V_{cc2}$ of the amplifier 51 is switched out. At the same time, the electronic switch 55 switches the output 54 to the electrical ground such that the electronic switch 55 acts as a discharge circuit 60. The charge stored in the coupling capacitor 58 is now exported via the electronic switch 55, something which is seen in a negative stimulation current $I_s$; see the jump in the time profile 61 of the stimulation current in FIG. 6, at the very bottom. The capacitor 58 is discharged exponentially until the charge in the coupling capacitor 58 has been completely extinguished.

It may further be mentioned that the strength of the stimulation current $I_S$ at the switching on instant $t=t_0$ is proportional to the amplitude $aV_D$ of the stimulation voltage.

Thus, switching the supply voltage $V_{cc2}$ on and off, as is achieved via the modulation of the injected IR light, firstly switches on the positive edge of the stimulation voltage $U_S$, whereupon a stimulation current $I_S$ flows. A negative stimulation current $I_S$ flows when the supply voltage $V_{cc2}$ is switched off, and this leads to a discharge of the capacitor 58.

The pulse length $t_1$ is in this case 500 µs, and the pulse spacing $t_2$ is 20 ms.

Figure 7:
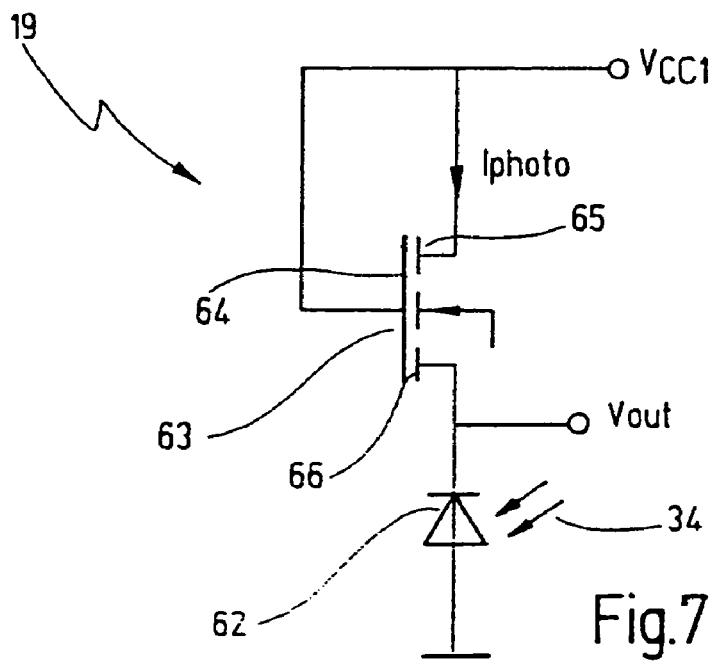
FIG. 7 shows a detailed illustration of the design of the image cell from FIG. 5.

An image cell 19 is illustrated in more detail in FIG. 7. Each image cell 19 has a photodiode 62 that is operated in the reverse-bias direction. The image cell 19 further has an nMOS transistor 63 whose gate electrode 64, interconnected with the drain electrode 65, is at $V_{cc1}$. At its source electrode 66, the nMOS transistor 63 is connected to the cathode of the photodiode 62, whose anode is at the electronic ground.

Owing to the interconnection shown, the nMOS transistor 63 operates below the threshold value, and so the voltage drop across the nMOS transistor 63 depends exponentially on the photocurrent $I_{photo}$, whose strength is determined, in turn, by the intensity of the visible light 34 that falls onto the photodiode 62.

Figure 8:
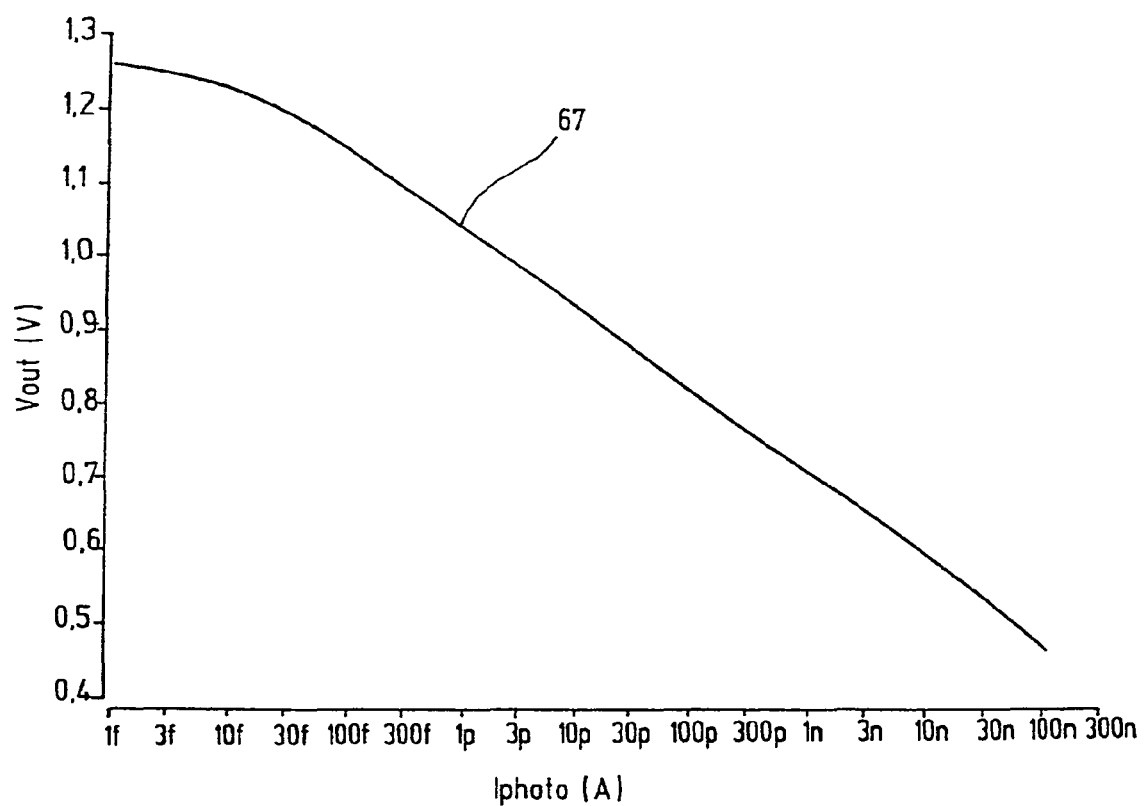
FIG. 8 shows the characteristic curve of the image cell from FIG. 7.

The result of this interconnection is that the output voltage $V_{out}$ of the image cell 19 from FIG. 7 is a logarithmic function of the intensity of the light 34, as is illustrated in FIG. 8 by the characteristic curve 67.

A circuit, comparable to the image cell 19 from FIG. 7, is used as image cell 23 for global brightness.

The differential voltage $V_D$ in FIG. 5 therefore represents the difference between the logarithms of the local and of the global image brightnesses. Since the global image brightness is determined by the mean brightness, which is a multiplicative variable in the local brightness, the mean brightness can be eliminated by the difference between the logarithm of the local and the logarithm of the global brightnesses as additive variable.

In this way, the respective pixel element 18 amplifies the contrast such that a high dynamic range is ensured and the retina implant can be adapted to different conditions of ambient lighting.

The invention claimed is:

1. An active retina implant with a multiplicity of pixel elements that convert incident light into electric stimulation signals for cells of the retina with which stimulation electrodes are to make contact, each pixel element having
at least one image cell that converts incident light into electric signals, and
at least one amplifier whose input is connected to the image cell and whose output is connected to at least one stimulation electrode to which it supplies a stimulation signal,
and with an energy supply which converts externally coupled external energy into a supply voltage for the image cells and the amplifiers,
wherein the image cell has a logarithmic characteristic according to which incident light of specific intensity is converted into electric signals of specific amplitude, wherein each pixel element has a logarithmic image cell for local image brightness, and each pixel element is assigned at least one logarithmic image cell for global brightness, and wherein the amplifier is designed as a differential amplifier of which one input is connected to the image cell for local image brightness, and of which the other input is connected to the image cell for global brightness.

2. The retina implant of claim 1, wherein the stimulation signal is supplied in the form of analog voltage pulses of specific pulse length and pulse spacings, the pulse amplitude being a function of the intensity of the incident light.

3. The retina implant of claim 2, wherein the output of the amplifier is connected to a controllable discharge circuit.

4. The retina implant of claim 2, wherein pulse length and pulse spacing are determined via the externally coupled external energy.

5. The retina implant of claim 3, wherein the image cells are supplied with a first voltage that differs from a second voltage with which the amplifiers are supplied.

6. The retina implant of claim 5, wherein the second voltage is switched on in step with a pulse length and a pulse spacing.

7. The retina implant of claim 6, wherein a discharge circuit is connected to a third voltage that is derived from the second voltage.

8. The retina implant of claim 1, wherein the image cells are supplied with a first voltage that differs from a second voltage with which the amplifiers are supplied.

9. The retina implant of claim 8, wherein the second voltage is switched on in step with a pulse length and a pulse spacing.

10. The retina implant of claim 8, wherein a discharge circuit is connected to a third voltage that is derived from the second voltage.

11. An active retina implant with a number of pixel elements that convert incident light into electric stimulation signals for cells of the retina with which stimulation electrodes are to make contact, each pixel element having
at least one image cell that converts incident light of specific intensity into electric signals, and
at least one amplifier whose input is connected to the image cell and whose output is connected to at least one stimulation electrode to which it supplies a stimulation signal, and with an energy supply which converts externally coupled external energy into a supply voltage for the image cells and the amplifiers, wherein the stimulation signal is supplied in the form of analog voltage pulses of specific pulse length and pulse spacings, the pulse amplitude being a function of the intensity of the incident light, and wherein pulse length and pulse spacing are determined via the externally coupled external energy.

12. The retina implant of claim 11, wherein the output of the amplifier is connected to a controllable discharge circuit.

13. The retina implant of claim 12, wherein the image cells are supplied with a first voltage that differs from a second voltage with which the amplifiers are supplied.

14. The retina implant of claim 13, wherein the second voltage is switched on in step with a pulse length and a pulse spacing.

15. The retina implant of claim 14, wherein a discharge circuit is connected to a third voltage that is derived from the second voltage.

16. The retina implant of claim 11, wherein the image cells are supplied with a first voltage that differs from a second voltage with which the amplifiers are supplied.

17. The retina implant of claim 16, wherein the second voltage is switched on in step with a pulse length and a pulse spacing.

18. The retina implant of claim 16, wherein a discharge circuit is connected to a third voltage that is derived from the second voltage.

19. The retina implant of claim 18, wherein each pixel element has a logarithmic image cell for local image brightness, and each pixel element is assigned at least one logarithmic image cell for global brightness.

20. The retina implant of claim 19, wherein the amplifier is designed as a differential amplifier of which one input is connected to the image cell for local image brightness, and of which the other input is connected to the image cell for global brightness.

21. The retina implant of claim 11, wherein each pixel element has a logarithmic image cell for local image brightness, and each pixel element is assigned at least one logarithmic image cell for global brightness.

22. The retina implant of claim 21, wherein the amplifier is designed as a differential amplifier of which one input is connected to the image cell for local image brightness, and of which the other input is connected to the image cell for global brightness.

* * * * *